(12) United States Patent
Montanari et al.

(10) Patent No.: US 6,232,348 B1
(45) Date of Patent: *May 15, 2001

(54) HYDROXYMETHYL DERIVATIVES OF 2-AMINO-1,2,3,4-TETRAHYDRONAPHTHALENE AS CARDIOVASCULAR AGENT

(75) Inventors: Stefania Montanari; Paolo Cavalleri; Francesco Santangelo, all of Milan; Cristina Fraire, Legnano; Giancarlo Grancini, Nova Milanese; Napoletano Mauro, Milan; Francesco Marchini, Lodi; Lorenzo Pradella, Cernusco Sul Naviglio; Claudio Semeraro, Bresso, all of (IT)

(73) Assignee: Zambon Group S.p.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/367,358

(22) PCT Filed: Feb. 4, 1998

(86) PCT No.: PCT/EP98/00588

§ 371 Date: Aug. 12, 1999

§ 102(e) Date: Aug. 12, 1999

(87) PCT Pub. No.: WO98/38154

PCT Pub. Date: Sep. 3, 1998

(30) Foreign Application Priority Data

Feb. 26, 1997 (IT) .................................. MI97A0415

(51) Int. Cl.⁷ ...................... A61K 31/135; C07C 211/00; C07C 213/00
(52) U.S. Cl. .......................... 514/647; 514/651; 564/336; 564/347
(58) Field of Search ..................... 564/336, 347; 514/647, 651

(56) References Cited

U.S. PATENT DOCUMENTS 5,070,106   12/1991   Casagrande et al. ............... 514/651
5,151,414   9/1992    Casagrande et al. ............... 514/114
5,407,956   4/1995    Santangelo et al. ............... 514/510
5,674,909   10/1997   Montanari et al. ................ 514/649
5,747,513   5/1998    Montanari et al. ................ 514/351

FOREIGN PATENT DOCUMENTS 0 321 968    6/1989   (EP).
93 19036     9/1993   (WO).
95 07885     3/1995   (WO).
96 08228A    3/1996   (WO).
98 38154     9/1998   (WO).

Primary Examiner—Howard C. Lee
Assistant Examiner—Leigh C. Maier
(74) Attorney, Agent, or Firm—Arent Fox Kintner Plotkin Kahn PLLC

(57) ABSTRACT

Compounds of formula (I)

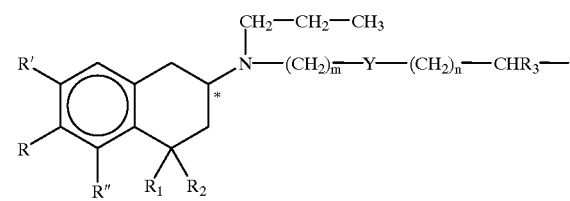

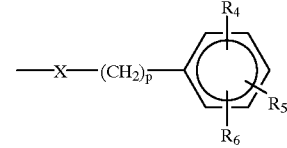

wherein R, R', R", $R_1$, $R_2$, $R_3$, $R_4$, $R_5$, $R_6$, X, Y, m, n, and p have the meanings reported in the description; and their pharmaceutically acceptable salts are described.

5 Claims, No Drawings

HYDROXYMETHYL DERIVATIVES OF 2-AMINO-1,2,3,4-TETRAHYDRONAPHTHALENE AS CARDIOVASCULAR AGENT

This application is a 371 of PCT/EP98/00588, filed Feb. 4, 1998.

The present invention relates to compounds active in the cardiovascular field, and in particular to hydroxymethyl derivatives of 2-amino-1,2,3,4-tetrahydronaphthalene and to the therapeutic use thereof The international patent application No.WO 96/08228 describes 2-amino-1,2,3,4-tetrahydronaphthalene derivatives of formula I

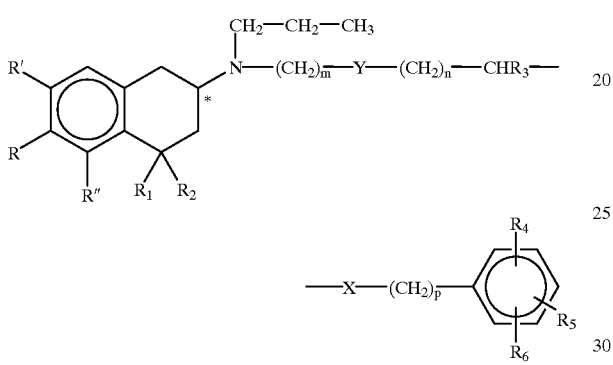

(I)

wherein
- m is an integer selected from 4, 5, 6, 7 and 8,
- R, R' and R" are hydrogen atoms or OH groups, provided that at least one of R, R' and R" is a hydrogen atom but R, R' and R" are not hydrogen atoms altogether at the same time and both R' and R" are not OH groups at the same time;
- or one of R' and R" is a NHCHO, NHCH$_3$, NHSO$_2$CH$_3$, CH$_2$OH or CH$_3$ group and the other is hydrogen;
- R$_1$ and R$_2$, the same or different, are hydrogen atoms, C$_1$–C$_3$ alkyl groups or, together with the carbon atom which they are bonded to, form a cyclopropyl group;
- n is an integer selected from 0, 1, 2, 3 and 4;
- p is an integer selected from 0 and 1;
- R$_3$ is a hydrogen atom or a C$_1$–C$_4$ alkyl group;
- Y is S, O, N(R$_7$)CO, CO(R$_7$)N or N(R$_7$);
- X is N(R$_8$), O, S, SO, SO$_2$, CO or a single bond;
- R$_4$, R$_5$ and R$_6$, the same or different, are hydrogen, OH, halogen, C$_1$–C$_4$ alkyl, C$_1$–C$_4$ alkoxy, nitro, C$_1$–C$_4$ alkylthio, NH$_2$, mono- or di-C$_1$–C$_4$ alkylamino, SH, C$_1$–C$_4$ alkylsulfonyl, C$_1$–C$_4$ alkoxycarbonyl, NHCHO, C$_1$–C$_4$ alkylcarbonylamino, NHCONH$_2$, C$_1$–C$_4$ alkylsulfonyamino, C$_1$–C$_4$ alkylaminosulfonyl, SO$_2$NH$_2$, NHSO$_2$NH$_2$, COOH, SO$_3$H, CONH$_2$, CH$_2$OH or phenyl; or
- R$_4$ and R$_5$, in ortho position each other, together form a chain of 3 or 4 groups selected from CR$^{III}$R$^{IV}$, CO, S, O and NR$^V$ wherein R$^{III}$ is a hydrogen atom or a C$_1$–C$_4$ alkyl group, R$^{IV}$ is a hydrogen atom, a C$_1$–C$_4$ alkyl group or an amino group and R$^V$ is a hydrogen atom or a C$_1$–C$_4$ alkyl group; or R$^{III}$ together with one of neighbouring R$^{III}$ or R$^V$ forms a single bond, or R$^V$ together with a neighbouring R$^{III}$ or R$^V$ forms a single bond;
- R$_7$ is a hydrogen atom or a C$_1$–C$_4$ alkyl group;
- R$_8$ is a hydrogen atom; or
- R$_7$ and R$_8$ together form a —CH$_2$— or —CH$_2$—CH$_2$— chain; or
- R$_4$, when in ortho position with respect to X, may form with R$_7$ a —CH$_2$— or —CH$_2$—CH$_2$— chain; or
- when X=O
- R$_4$, when in ortho position with respect to X, may form with R$_3$ a —CH$_2$—O— chain;
- the asterisk marks an asymmetric carbon atom;

provided that
- a) when p=1, X is a N(R$_8$) group;
- b) when Y is N(R$_7$). R$_7$ is hydrogen or alkyl and R$_3$ is hydrogen, at least one of R$_4$, R$_5$ and R$_6$ is different from hydrogen, halogen, C$_1$–C$_4$ alkyl and C$_1$–C$_4$ alkoxy;
- c) when Y is N(R$_7$), R$_7$ is hydrogen or alkyl, R$_3$ is hydrogen and X is a single bond, at least one of R$_4$, R$_5$ and R$_6$ is different from hydrogen, halogen, NH$_2$, C$_1$–C$_4$ alkyl, C$_1$–C$_4$ alkoxy and nitro;
- d) when Y is N(R$_7$), R$_7$ is hydrogen or alkyl, n is 1, R$_3$ is hydrogen and X is a single bond, at least one of R$_4$, R$_5$ and R$_6$ is different from hydrogen and OH;

and the pharmaceutically acceptable salts thereof

These compounds are agonists of the dopaninergic receptors more potent than dopamine and other known compounds, are substantially deprived of interaction with other receptors and are orally bioavailable with a long term of action.

It has been now found that a selected sub-class of compounds of formula I is endowed with an activity profile in the cardiovascular field so peculiar that it is surprisingly distinguished from the compounds comprised in the above cited patent application. This peculiarity resides in the higher bioavailability that this restricted class characterised by the presence of a hydroxymethyl moiety on the tetrahydronaphthalene ring, shows with respect to the corresponding derivatives lacking of such moiety. Therefore the present invention relates to compounds of formula II

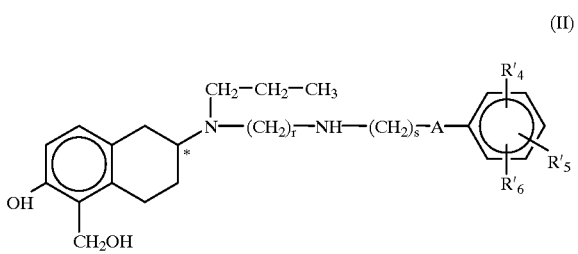

(II)

wherein
- r is an integer selected from 5, 6 and 7;
- s is an integer selected from 2 and 3;
- A is O or a single bond;
- R'$_4$, R'$_5$ and R'$_6$, the same or different, are hydrogen, OH, halogen, nitro, C$_1$–C$_4$ alkyl, C$_1$–C$_4$ alkoxy, C$_1$–C$_4$ alkylthio, NH$_2$, mono- or di-C$_1$–C$_4$ alkylamino, SH, C$_1$–C$_4$ alkylsulfonyl, C$_1$–C$_4$ alkoxycarbonyl, NHCHO, C$_1$–C$_4$ alkylcarbonylamino, NHCONH$_2$, C$_1$–C$_4$ alkylsulfonylamino, C$_1$–C$_4$ alkylaminosulfonyl, SO$_2$NH$_2$, NHSO$_2$NH$_2$, COOH, SO$_3$H, CONH$_2$, CH$_2$OH or phenyl; or
- R'$_4$ and R'$_5$, in ortho position each other, together form a chain of 3 or 4 groups selected from CT'T", CO, S, O and NT''', wherein T' is a hydrogen atom or a $C_1$–$C_4$ alkyl groups, T'' is a hydrogen atom, a $C_1$–$C_4$ alkyl group or an amino group and T''' is a hydrogen atom or a $C_1$–$C_4$ alkyl group; or T' together with a neighbouring T'' or T''' forms a single bond, or T'' together with a neighbouring T' or T''' forms a single bond;

the asterisk marks an asymmetric carbon atom;

and the pharmaceutically acceptable salts thereof.

The compounds of formula II have at least an asymmetric centre marked by an asterisk, and then may be in form of stereoisomers.

Object of the present invention are compounds of formula II in form of stereoisomeric mixture so as in form of single stereoisomers.

Preferred compounds of formula II are those wherein the carbon atom marked by an asterisk has the S configuration.

The compounds of formula II are agonists of the dopaminergic receptors, also orally active. They are therapeutically effective in the cardiovascular field, especially in the treatment of arterial hypertension, heart and renal failure, in the treatment of peripheral arteriopathies, arrhythmia, cerebrovascular insufficiencies and ischemic cardiopathy. Their bioavailability is substantially higher than the one of the compounds of the international patent application No.WO96/08228 and this feature makes their use profitable as yielding a more constant effect in different groups of patients, mainly in case of even minoi or physiologic troubles in the organs involved in the first step metabolism.

The term halogen atom means a fluorine, chlorine, bromine or iodine atom. Specific examples of alkyl or alkoxy groups are methyl, ethyl, n-propyl, i-propyl, n-butyl, s-butyl, tertbutyl, methoxy, ethoxy, n-propoxy, i-propoxy, n-butoxy and i-butoxy.

Hereinbelow specific examples of optionally unsaturated chain made of 3 or 4 groups selected from CT'T'', CO, S, O and NT''' are provided: —O—CHT'—O—, —S—CO—NT'''—, —CHT'—CO—NT'''—, —S—CT''=N—, —O—CO—NT''', —CO—NT'''—NT''', —NT'''—CO—NT'''—.

Preferred compounds of formula II are those wherein the carbon atom marked by an asterisk has the S configuration.

Even more preferred are the compounds wherein r is 6 and the carbon atom marked by an asterisk has the S configuration.

Among the meanings of $R'_4$ and $R'_5$ and $R'_6$ hydrogen, hydroxy, methoxy, methyl, nitro, chloro, methylsulfonyl, $NH_2$, $SO_2NH_2$, methysulfonylamino, $NHCONH_2$, methoxycarbonyl, acetylamino, $CONH_2$, $CH_2OH$ and $SO_3H$ or, when $R'_4$ and $R'_5$ in ortho position each other form a chain, a group of formula —S—CONT'''—wherein T''' is a hydrogen atom, or methylendioxy are preferred.

Pharmaceutically acceptable salts of the compounds of formula II are those with organic or inorganic acids such as, for example, hydrochloric, hydrobromic, hydroiodic, nitric, sulphuric, phosphoric, acetic, benzoic, maleic, fumaric, succinic, tartaric, citric, aspartic, methansulfonic and 3,7-di-tert.butylnaphthalen-1,5-disulfonic (dibudinic acid), xinafoic. The hydrochloride is the preferred salt.

The preparation of the compounds of formula II may be effected following the synthesis methods hereinbelow.

The compounds of formula II may be obtained starting from a naphthylamine, optionally in form of salt, of formula III

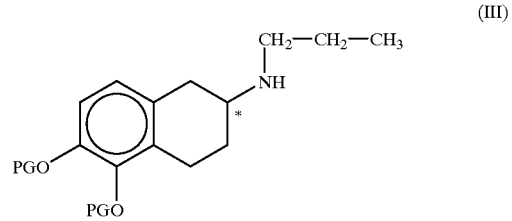

wherein PG are protecting groups suitable to the hydroxy moiety such as benzyl and methyl, which is prepared, for example, as described in the international patent application No. WO 95/07885. This compound is protected on the amino moiety by a protecting group suitable to this residue such as, for example, trifluoroacetyl, in the presence of a base such as, for example, a alkali metal carbonate or triethylamine, and subsequently the deprotection in 5-position effected with iodotrimethylsilane to yield a compound of formula IV

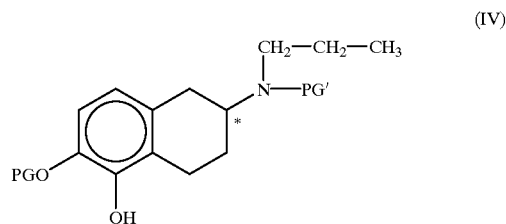

wherein PG is as defined above and PG' is a protecting group which is then orthogonally removed in a suitable manner and substituted by a new protecting group PG'' for the amino moiety different from PG' such as, for example, tert.butoxycarbonyl, to give a compound of formula V

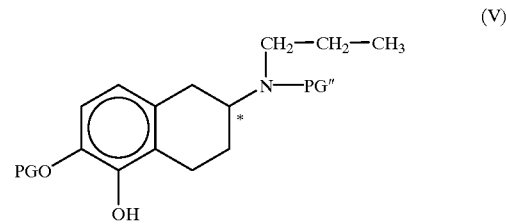

wherein PG and PG'' are as defined above.

Alternatively the compound of formula III may be deprotected in 5-position without previous protection of its amino moiety. In this way the amino moiety is directly protected with the protecting group PG'' after such deprotection in 5-position.

The hydroxy moiety of the compound of formula V is transformed into a triflate group by a reaction with, for example, N-phenyltrifluorometansulfonimide or trifluorometansulfonic anhydride, then carbonylated with carbon monoxide in the presence of a transition metal catalyst, preferably palladium acetate, and of a binding agent such as, for example, 1,3-bisdiphenylphosphinopropane, 1,4-bisdiphenylphosphinobutane, to yield a compound of formula VI

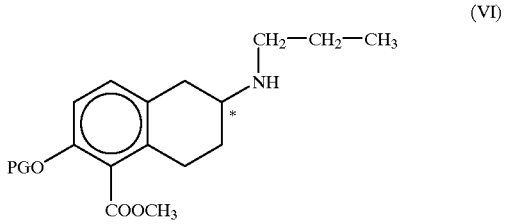

(VI)

wherein PG is as defined above. Said compound VI is reacted with an acid of formula VII

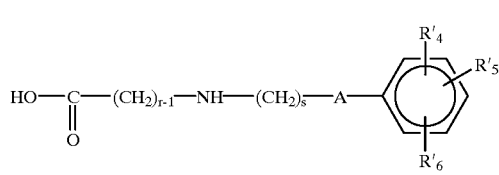

(VII)

wherein r, s, A, R'$_4$, R'$_5$ and R'$_6$ have the above cited meanings, or with a reactive derivative thereof such as an acyl halide or a mixed anhydride which may be optionally prepared in situ, in an inert solvent in the presence of a base such as an alkali carbonate or hydrogenocarbonate or a tertiary amine, to yield an intermediate of formula VIII

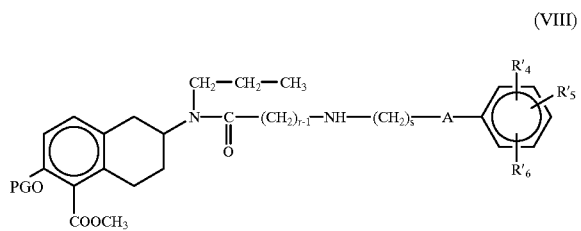

(VIII)

wherein PG, r, Z, s, A, R'$_4$, R'$_5$ and R'$_6$ are as defined above, which is first deprotected on the hydroxy group in 6-position, and subsequently reduced on the amidic and ester groups with a reducing agent such as borane methylsulfide or lithium aluminium hydride, to give the compounds of formula II.

The compounds of formula II in an optically active form are obtained by optical separation or by means of stereospecific or stereoselective synthesis.

The preparation of the salts of the compounds of formula II is carried out according to conventional methods.

The compounds of formula II are agonist of the dopaminergic receptors D$_1$ and D$_2$ like the other compounds of the international patent application No. WO 96/08228 as shown in the in vitro activity tests on receptors D$_1$ and D$_2$ (example 14). The tests of interaction with other receptors showed that the compounds of formula II do not significantly interact and thus they are endowed with high specificity.

The compounds of formula II also showed to be inactive in the central nervous system by oral administration and the absence of such an effect is a further positive feature. It is clear that these features of receptorial selectivity and specificity joined to the lack of activity on the central nervous system make the compounds of formula II especially suitable for the treatment of cardiovascular diseases and mainly in the antihypertensive therapy, in the therapy of the heart and renal failure, in the treatment of peripheral arteriopathy, arrhythmia, cerebrovascular insufficiencies and ischemic cardiopathy.

Beside the already stressed superior pharmacological activity, the feature which most characterizes the compounds of formula II, object of the invention, is their oral bioavailability surprisingly higher than the one of the other compounds of the international patent application No. WO 96/08228. Actually the increased bioavailability of the compounds of the invention yields higher plasmatic concentration and a greater homogeneity of the effect in different groups of patients.

It follows that for the practical therapeutical uses, the compounds of formula II may be administered both parenterally and enterally differing from dopamine and dopexamine.

The therapeutic doses will be generally comprised between 1 and 100 mg per day and between 0.5 and 50 mg for single oral administration.

Therefore a further object of the present invention are the pharmaceutical composition containing a therapeutically effective amount of the compounds of formula II or of the pharmaceutically acceptable salts thereof in admixture with a suitable carrier. The pharmaceutical compositions object of the invention may be liquid, suitable for enteral or parenteral administration, and, preferably, solid such as tablets, capsules, granulates suitable for the oral administration.

The preparation of the pharmaceutical compositions object of the invention may be carried out according to common techniques.

For better illustrating the present invention the following examples are now provided. The chromatographic purification were effected on silica gel column (230–400 mesh). Unless otherwise mentioned, the mass spectra were carried out under the following conditions: chemical ionization, isobutane, positive ions.

EXAMPLE 1

Preparation of (S)—N—(6-benzyloxy-5-hydroxy-1,2,3,4-tetrahydro-2-naphthyl)-N-propyl-trifluoroacetamide A suspension of (S)-N-propyl-5,6-dibenzyloxy-1,2,3,4-tetrahydro-2-naphthylamine hydrochloride (5 g; 11.42 mmoles) and triethylamine (4.2 ml; 28.57 mmoles) in methylene chloride (100 ml), kept under stirring at room temperature, was dropwise added with a solution of trifluoroacetic anhydride (1.7 ml; 12 mmoles) in methylene chloride (20 ml). After 30 minutes water was added (100 ml). The phases were separated and the organic one was washed first with a 1N solution of HCl (100 ml) then with water (100 ml), anhydrified over Na$_2$SO$_4$ and the solvent was evaporated under reduced pressure. The crude was dissolved in chloroform (60 ml) and the solution was dropwise added, under stirring at room temperature, with iodotrimethylsilane (2.44 ml; 17.13 mmoles). After 3 hours the reaction mixture was poured into methanol (200 ml) and the solvents were evaporated under reduced pressure. The residue was added with methylene chloride (200 ml) and water (150 ml). The phases were separated and, the organic one was washed first with a 5% solution of sodium thiosulfate (150 ml) and then with a saturated solution of NaCl (150 ml), anhydrified over sodium sulfate and the solvent was evaporated under reduced pressure. The resulting crude was purified by silica gel chromatography (eluent: petrolatum: ethyl acetate =8:2).

There were obtained 3.4 g of (S)—N—(6-benzyloxy-5-hydroxy-1,2,3,4-tetrahydro-2-naphthyl)-N-propyl-trifluoroacetamide.

$^1$H-NMR (200 MHz, CDCl$_3$) δ (ppm): 0.91 and 0.92 (2t, 3H); 1.57–2.31 (m, 4H); 2.58–3.39 (m, 6H); 4.02–4.24 (2m, 1H); 5.08 (2s, 2H); 5.73 and 5.76 (2s, 1H); 6.55 and 6.57 (2d, 1H); 6.75 and 6.77 (2d, 1H); 7.29–7.43 (m, 5H). Mass: 408 (M+H)$^+$.

EXAMPLE 2
Preparation of (S)-N-propyl-6-benzyloxy-5-hydroxy-1,2,3,4-tetrahydro-2-naphthylamine A suspension of (S)-N-(6-benzyloxy-5-hydroxy-1,2,3,4-tetrahydro-2-naphthyl)-N-propyl-trifluoroacetamide (1 g; 2.45 mmoles), prepared as described in example 1, in methanol (10 ml) was added, under stirring at room temperature, with a solution of NaOH (0.4 g; 9.83 mmoles) in water (0.6 ml). The reaction mixture was heated to reflux for 3.5 hours, then left at room temperature overnight. After cooling to 0° C. ethyl ether saturated with gaseous HCl was added until total acidification and the solvents were evaporated under reduced pressure. The residue was added with ethyl acetate and a 5% solution of ammonia. The phases were separated and the organic one was washed with water, anhydrified over $Na_2SO_4$ and the solvent evaporated under reduced pressure.

There were obtained 740 mg of (S)-N-propyl-6-benzyloxy-5-hydroxy-1,2,3,4-tetrahydro-2-naphthylamine.

$^1$H-NMR (200 MHz, CDCl$_3$) δ (ppm): 0.93 (t, 3H); 1.41–1.67 (m, 3H); 1.98–2.14 (m, 1H); 2.41–3.03 (m, 7H); 5.05 (s, 2H); 6.54 (d, 1H); 6.72 (d, 1H); 7.27–7.41 (m, 5H). Mass: 312 (M+H)$^+$.

EXAMPLE 3
Preparation of (S)-N-(tert.butoxycarbonyl)-N-propyl-6-benzyloxy-5-hydroxy-1,2,3,4-tetrahydro-2-naphthylamine A solution of (S)-N-propyl-6-benzyloxy-5-hydroxy-1,2,3,4-tetrahydro-2-naphthylamine (1 g; 3.2 mmoles), prepared as described in example 2, in methylene chloride (10 ml) was dropwise added, under stirring at room temperature, with a solution of di-(tertbutyl)-hydrogenocarbonate (0.74 g; 3.37 mmoles) in methylene chloride (2 ml). After 4 hours water and methylene chloride were added, the phases were separated and the organic one was washed with water, anhydrified over $Na_2SO_4$ and evaporated to dryness under reduced pressure.

There was obtained 1.3 g of (S)-N-(tert.butoxycarbonyl)-N-propyl-6-benzyloxy-5-hydroxy-1,2,3,4-tetrahydro-2-naphthylamine.

$^1$H-NMR (200 MHz, CDCl$_3$) δ (ppm): 0.87 (t, 3H), 1.45 (s, 9H); 1.42–2.07 (m, 4H); 2.52–3.14 (m, 6H), 3.92–4.28 (m, 1H); 5.06 (s, 2H), 5.70 (bs, 1H); 6.52 (d, 1H); 6.72 (d, 1H); 7.28–7.42 (m, 5H). Mass (electronic impact) : 411 (M)$^+$

EXAMPLE 4
Preparation of (S)-N-(tert.butoxycarbonyl)-propyl-6-benzyloxy-5-trifluoromethyl-sulfonyloxy-1,2,3,4-tetrahydro-2-naphthylamine A solution of (S)-N-(tert.butoxycarbonyl)-N-propyl-6-benzyloxy-5-hydroxy-1,2,3,4-tetrahydro-2-naphthylamine (1 g; 2.43 mmoles), prepared as described in example 3, in acetonitrile (40 ml) was added at room temperature with $K_2CO_3$ (670 mg; 4.86 mmoles) and, dropwise, with a solution of N-phenyltrifluoromethansulfonimide (1.04 g; 2.92 mmoles) in acetonitrile (5 ml). The reaction mixture was heated to 55° C. for 19 hours, then the solvent was evaporated under reduced pressure. The residue was added with methylene chloride and water. The phases were separated and the organic one was washed with water, anhydrified over $Na_2SO_4$ and the solvent evaporated under reduced pressure. The resulting crude was purified by silica gel chromatography (eluent: petrolatum:ethyl acetate=95:5).

There was obtained 1 g of (S)-N-(tert.butoxycarbonyl)-N-propyl-6-benzyloxy-5-trifluoromethylsulfoniloxy-1,2,3,4-tetrahydro-2-naphthylamine.

$^1$H-NMR (200 MHz, CDCl$_3$) δ (ppm): 0.87 (t, 3H); 1.45 (s, 9H); 1.48–2.09 (m, 4H); 2.66–3.13 (m, 6H); 3.89–4.22 (m, 1H), 5.12 (s, 2H); 6.80 (d, 1H); 6.95 (d, 1H); 7.27–7.44 (m, 5H). Mass (thermospray): 544 (M+H)$^+$.

EXAMPLE 5
Preparation of (S)-N-propyl-6-benzyloxy-5-methoxycarbonyl-1,2,3,4-tetrahydro-2-naphthylamine hydrochloride A solution of (S)-N-(tert.butoxycarbonyl)-N-propyl-6-benzyloxy-5-trifluoromethyl-sulfoniloxy-1,2,3,4-tetrahydro-2-naphthylamine (8.97 g, 16.52 mmoles), prepared as described in example 4, in dimethylsulfoxide (53 ml) and methanol (21 ml) was added, under $N_2$ at room temperature, with triethylamine (4.6 ml; 33 mmoles), palladium acetate (222 mg; 0.99 mmole) and 1,3-bisdiphenylphosphinopropane (409 mg; 0.99 mmole). The reaction mixture was then heated to 70° C. under CO pressure (8 bar) for 48 hours. After cooling to room temperature the mixture was poured water and ethyl acetate. The phases were separated and the organic one was washed with water, anhydrified over $Na_2SO_4$ and evaporated to dryness under reduced pressure. The residue was dissolved in ethyl acetate (80 ml) and the solution was added, under stirring at room temperature, with ethyl acetate saturated with gaseous HCl (110 ml). After 3 hours the formed precipitate was filtered over a porous partition and dried under vacuum at 40° C. The resulting solid was treated under reflux with a mixture of 95° ethanol (85 ml) and water (5 ml). After hot filtering off of the insoluble and cooling to room temperature a precipitate was obtained and filtered over a porous partition, washed over the filter with ethyl acetate and dried under vacuum at 40° C.

There were obtained 3.8 g of (S)-N-propyl-6-benzyloxy-5-methoxycarbonyl-1,2,3,4-tetrahydro-2-naphthylamine hydrochloride.

$^1$H-NMR (200 MHz, DMSO-$_6$) δ (ppm): 0.93 (t, 3H); 1.56–2.31 (m, 4H), 2.61–3.22 (m, 6H); 3.31–3.49 (m, 1H); 3.79 (s, 3H); 5.13 (s, 2H); 6.99 (d, 1H); 7.15 (d, 1H); 7.22–7.39 (m, 5H). Mass (thermospray): 354 (M+H)$^+$.

EXAMPLE 6
Preparation of (S) 6-N-propyl-N-(6-((4-methylsylfonylphenyl)acetylamino)-1-ketohexyl)amino-6-benzyloxy-5-methoxycarbonil-1,2,3,4-tetrahydro-2-naphthylamine A suspension of 6-(4-methylsulfonylphenyl) acetamidohexanoic acid (1.38 g; 4.23 mmoles) in methylene chloride (13 ml) was added, under stirring at room temperature, with thionyl chloride (0.37 ml; 5.07 mmoles). After 1 hour the solvent and the thionyl chloride in excess were evaporated under reduced pressure. The resulting oil was dissolved in methylene chloride (5 ml) and the solution was dropwise added, under stirring at room temperature, with a solution of (S)-N-propyl-6-benzyloxy-5-methoxycarbonyl-1,2,3,4-tetrahydro-2-naphthylamine hydrochloride (1.5 g; 3.84 mmoles), prepared as described in example 5, and triethylamine (1.2 ml; 8.6 mmoles) in methylene chloride (15 ml). After 40 minutes the reaction mixture was added with water. The phases were separated and the organic one was washed first with 10% CHl then with a 5% solution of NaHCO$_3$ and finally with a saturated solution of NaCl, anhydrified over $Na_2SO_4$ and evaporated to dryness under reduced pressure. There were obtained 2.5 g of (S) 6-N-propyl-N-(6-((4-methylsulfonylphenyl)-acetylamino)-1-ketohexyl)amino-6-benzyloxy-5-methoxycarbonyl-1,2,3,4-tetrahydro-2-naphthylamine.

$^1$H-NMR (200 MHz, CDCl$_3$) δ (ppm): 0.88 and 0.91 (2t, 3H); 1.21–2.07 (m, 10H); 2.25–2.41 (m, 2H); 2.65–3.37 (m, 8H); 3.00 and 3.01 (2s, 3H); 3.58 and 3.59 (2s, 2H); 3.85 and 3.88 (2s, 3H); 3.86–4.07 and 4.40–4.59 (2m, 1H); 5.07 and 5.08 (2s, 2H); 6.41 (m, 1H); 6.73 and 6.77 (2d, 1H); 6.97 and 7.02 (2d, 1H); 7.23–7.4 (m, 5H); 7.41–7.90 (m, 4H). Mass: 663 (M+H)$^+$.

EXAMPLE 7
Preparation of (S)-N-propyl-N-(6-(2-(4-methylsulfonylphenyl)ethylamino)hexyl)-5-hydroxymethyl-6-hydroxy-1,2,3,4-tetrahydro-2-naphthylamine A solution of (S) 6-N-propyl-N-{6-[(4-methylsulfonylphenyl)acetylamino]-1-ke-tohexyl}amino-6-benzyloxy-5-methoxycarbonyl-1,2,3,4-tetrahydro-2-naphthylamine (0.5 g, 0.75 mmole), prepared as described in example 6, in absolute ethanol (10 ml) was maintained under stirring at room temperature under hydrogen pressure (50 psi) in the presence of 10% Pd/C (0.3 g) for 3.5 hours. After filtering off the catalyst the reaction mixture was evaporated to dryness under reduced pressure. The residue dissolved in dry tetrahydrofiran (8 ml) was dropwise added at room temperature with borane methylsulfide (0.42 ml; 4.3 mmoles), then the reaction mixture was heated to reflux for 1.5 hours. After cooling to room temperature further borane methylsulfide was added (0.27 ml. 2.8 mmoles). The reaction mixture was again heated to reflux for 1.5 hours. After cooling to 5° C. a 1:1 mixture of acetic acid and water (6 ml) was dropwise added, then the reaction mixture was again heated to reflux for 30 minutes. The residue obtained after evaporation of the solvents under reduced pressure was dissolved in methanol and the solution was evaporate again. The resulting crude was purified by silica gel chromatography (eluent: methylene chloride:methanol:30% ammonia in a gradient from 95:5:0.5 to 90:10:1).

There were obtained 250 mg of (S)-N-propyl-N-(6-(2-(4-methylsulfonylphenyl)ethylamino)hexyl)-5-hydroxymethyl-6-hydroxy-1,2,3,4-tetrahydro-2-naphthylamine.

$^1$H-NMR (200 MHz, CDCl$_3$) δ (ppm): 0.85 (t, 3H); 1.21–2.04 (m, 12H); 2.42–2.92 (m, 15H); 3.01 (s, 3H); 4.82 and 4.86 (2d, 2H, AB system); 6.62 (d, 1H); 6.84 (d, 1H); 7.35–7.85 (m, 4H). Mass (thermospray): 5 7 (M+H)$^+$.

The corresponding dimaleate salt was prepared by dissolution of the product in ethyl acetate, addition of 2 equivalents of maleic acid dissolved in ethyl acetate and evaporation of the solvent under reduced pressure.

$^1$H-NMR (200 MHz, D$_2$O) δ (ppm): 0.81 (t, 3H); 1.23–2.20 (m, 12H); 2.60–3.24 (m, 14H); 3.09 (s, 3H); 3.48–3.63 (m, 1H); 4.53 (s, 2H); 6.09 (s, 4H); 6.63 (d, 1H); 6.87 (d, 1H); 7.39–7.79 (m, 4H). Mass (thermospray): 517 (M+H)$^+$. Elemental analysis: calculated C59.34, H 7.00, N 3.74; found C 59.08, H 7.4, N 3.72.

EXAMPLE 8
Preparation of (S)-N-propyl-6-methoxy-5-hydroxy-1,2,3,4-tetrahydro-2-naphthylamine A suspension of (S) N-propyl-5,6-dimetossi-1,2,3,4-tetrahydro-2-naphthylamine hydrobromide (2 g; 6.06 mmoles), in chloroform (40 ml) was dropwise added, under stirring at room temperature, with iodotrimethylsilane (3 ml; 21.2 mmoles). After 16 hours the reaction mixture was poured in methanol and the solvents were evaporated under reduced pressure. The residue was added with methylene chloride and a 5% solution of NaHCO$_3$. The phases were separated and the organic one was washed first with a 5% solution of sodium thiosulfate and then with a 5% solution of NaHCO$_3$, anhydrified over Na$_2$SO$_4$ and the solvent was evaporated under reduced pressure. The resulting crude was purified by silica gel chromatography (eluent: methylene chloride: :methanol:30% ammonia=95:5:0.5).

There were obtained 1.13 g of (S)-N-propyl-6-methoxy-5-hydroxy-1,2,3,4-tetrahydro-2-naphthylamine.

$^1$H-NMR (200 MHz, CDCl$_3$) δ (ppm): 0.93 (t, 3H); 1.43–1.68 (m, 3H); 2.00–2.15 (m, 1H); 2.44–3.02 (m, 7H); 3.83 (s, 3H); 6.56 (d, 1H); 6.67 (d, 1H). Mass (electronic impact): 235 (M)$^+$

EXAMPLE 9
Preparation of (S)-N-(tert.butoxycarbonyl)-N-propyl-6-methoxy-5-hydroxy-1,2,3,4-tetrahydro-2-naphthylamine A solution of (S)-N-propyl-6-methoxy-5-hydroxy-1,2,3,4-tetrahydro-2-naphthylamine (1.05 g, 4.46 mmoles), prepared as described in example 8, in dimethylformamide (10 ml) was dropwise added, under stirring at room temperature, with a solution of di-(tertbutyl)-dicarbonate (0.97 g; 4.46 mmoles) in dimethylformamide (3 ml). After 1 hour water and ethyl ether were added, the phases were separated and the organic one was washed with water, anhydrified over Na$_2$SO$_4$ and evaporated to dryness under reduced pressure.

There were obtained 1.42 g of (S)-N-(tert.butoxycarbonyl)-N-propyl-6-methoxy-5-hydroxy-1,2,3,4-tetrahydro-2-naphthylamine.

$^1$H-NMR (200 MHz, CDCl$_3$) δ (ppm): 0.87 (t, 3H), 1.46 (t, 9H), 1.49–2.07 (m, 4H); 2.52–3.16 (m, 6H); 3.84 (s, 3H); 3.90–4.31 (m, 1H); 5.66 (bs, 1H), 6.55 (d, 1H); 6.68 (d, 1H). Mass (electronic impact): 335 (M)$^+$

EXAMPLE 10
Preparation of (S)-N-(tert.butoxycarbonyl)-N-propyl-6-methoxy-5-methoxycarbonyl-1,2,3,4-tetrahydro-2-naphthylamine A solution of (S)-N-(tert.butoxycarbonyl)-N-propyl-6-methoxy-5-hydroxy-1,2,3,4-tetrahydro-2-naphthylamine (1.4 g; 4.17 mmoles), prepared as described in example 9, in acetonitrile (42 ml) was added at room temperature with K$_2$CO$_3$ (1.15 g, 8.34 mmoles) and, dropwise, with a solution of N-phenyltrifluoromethansulfonimide (1.78 g; 5 mmoles) in acetonitrile (10 ml). The reaction mixture was heated to 55° C. for 19 hours, then the solvent was evaporated under reduced pressure. The residue was added with methylene chloride and water. The phases were separated and the organic one was washed with water, anhydrified over Na$_2$SO$_4$ and the solvent evaporated under reduced pressure. The residue was dissolved in dimethylsulfoxide (13 ml) and methanol (5 ml) and the solution was added, under N$_2$ at room temperature, with triethylamine (1.1 ml, 7.87 mmoles), palladium acetate (53 mg; 0.236 mmole) and 1,3-bisdiphenylphosphinopropane (97 mg; 0.236 mmole). The reaction mixture was then heated to 70° C. under CO pressure (9 bar) for 90 hours during which further palladium acetate (18 mg, 0.080 mmole) and 1,3-bisdiphenylphosphinopropane (33 mg, 0.080 mmole) were added in one portion. After cooling to room temperature the mixture was poured into water and methylene chloride. The phases were separated and the organic one was washed with water, anhydrified over Na$_2$SO$_4$ and evaporated to dryness under reduced pressure. The resulting crude was purified by silica gel chromatography (eluent: petrolatum:ethyl acetate=90:10).

There was obtained 1.08 g of (S)-N-(tert.butoxycarbonyl)-N-propyl-6-methoxy-5-methoxycarbonyl-1,2,3,4-tetrahydro-2-naphthylamine.

$^1$H-NMR (200 MHz, CDCl$_3$) δ (ppm): 0.86 (t, 3H), 1.44 (t, 9H); 1.46–2.00 (m, 4H); 2.71–3.13 (m, 6H); 3.78 (s, 3H); 3.89 (s, 3H), 3.90–4.27 (m, 1H); 6.71 (d, 1H); 7.03 (d, 1H). Mass (electronic impact): 377 (M)$^+$

EXAMPLE 11
Preparation of (S)-N-propyl-6-methoxy-5-methoxycarbonyl-1,2,3,4-tetrahydro-2-naphthylamine hydrochloride A solution of (S)-N-(tert.butoxyvcarbonyl)-N-propyl-6-methoxy-5-methoxycarbonyl-1,2,3,4-tetrahydro-2-naphthylamine (1.06 g, 2.81 mmoles), prepared as described in example 10, in ethyl acetate (12 ml) was added, under stirring at room temperature, with ethyl acetate saturated with gaseous HCl (5 ml). After 16 hours the mixture was cooled to 0° C. and the formed precipitate was filtered on a porous partition, washed on the filter with ethyl acetate and ethyl ether and dried under vacuum at 50° C.

There was obtained 0.79 g of (S)-N-propyl-6-methoxy-5-methoxycarbonyl-1,2,3,4-tetrahydro-2-naphthylamine hydrochloride.

$^1$H-NMR (200 MHz, DMSO-$d_6$) δ (ppm): 0.94 (t, 3H); 1.56–2.32 (m, 4H); 2.61–3.26 (m, 6H); 3.30–3.49 (m, 1H); 3.73 (s, 3H); 3.79 (s, 3H); 6.93 (d, 1H); 7.19 (d, 1H); 9.10 (broad signal, 2H). Mass (electronic impact): 277 (M)$^+$

EXAMPLE 12

Preparation of (S) 6-N-propyl-N-{6-[(4-methylsulfonylphenyl)acetylamino]-1-ketohexyl}amino-6-methoxy-5-methoxycarbonyl-1,2,3,4-tetrahydro-2-naphthylamine A suspension of 6-(4-methylsulfonylphenyl)acetamidohexanoic acid (0.88 g; 2.7 moles) in methylene chloride (8 ml) was added, under stirring at room temperature, with thionyl chloride (235 ml; 3.2 mmoles). After 1 hour the solvent and the thionyl chloride in excess were evaporated under reduced pressure. The resulting oil was dissolved in methylene chloride (5 ml) and the solution was dropwise added, under stirring at room temperature, to a solution of (S)-N-propyl-6-methoxy-5-methoxycarbonyl-1,2,3,4-tetrahydro-2-naphthylamine hydrochloride (0.76 g; 2.43 mmoles), prepared as described in example 11, and triethylamine (0.75 ml; 5.4 mmoles) in methylene chloride (10 ml). After 30 minutes the mixture was added with water. The phases were separated and the organic one was washed first with 1N HCl, then with a 5% solution of NaHCO$_3$ and at last with a saturated solution of sodium chloride, anhydrified over sodium sulfate and evaporated to dryness under reduced pressure. There were obtained 2.5 g of (S) 6-N-propyl-N-{6-[(4-methylsulfonylphenyl)acetyl-amino]-1-ketohexyll}amino-6-benzyloxy-5-methoxycarbonyl-1,2,3,4-tetrahydro-2-naphthylamine. The resulting crude was purified by silica gel chromatography (eluent: methylene chloride:methanol=97:3).

There were obtained 1.29 g of (S) 6-N-propyl-N-{6-[(4-methylsulfonylphenyl)-acetylamino]-1-ketohexyl}amino-6-benzyloxy-5-methoxycarbonyl-1,2,3,4-tetrahydro-2-naphthylamine.

$^1$H-NMR (200 MHz, CDCl$_3$) δ (ppm): 0.87 and 0.90 (2t, 3H); 1.20–2.05 (m, 10H); 2.27–2.40 (m, 2H); 2.66–3.37 (m, 8H); 3.01 (s, 3H); 3.59 and 3.60 (2s, 2H); 3.78 and 3.79 (2s, 3H); 3.86 and 3.89 (2s, 3H); 3.90–4.08 and 4.40–4.60 (2m, 1H); 6.39 (m, 1H); 6.68–7.11 (4d, 2H), 7.41–7.92 (m, 4H). Mass (electrospray, positive ions): 587 (M+H)$^+$

EXAMPLE 13

Preparation of (S)-N-propyl-N-{6-[2-(4-methylsulfonylphenyl)ethylamino]hexyl}-5-hydroxymethyl-6-hydroxy-1,2,3,4-tetrahydro-2-naphthylamine A solution of (S) 6-N-propyl-N-{6-[(4-methylsulfonylphenyl)acetylamino]-1-ketohexyl}amino-6-methoxy-5-methoxycarbonyl-1,2,3,4-tetrahydro-2-naphthylamine (100 mg; 0.17 mmole), prepared as described in example 12, in chloroform (3 ml) was added, under stirring at 0° C., with a 1M solution of boron tribromide in methylene chloride (0.43 ml; 0.43 mmole). At the end of the addition the temperature was left to rise till room temperature. After 2 hours the reaction mixture was heated to 50° C. for 2.5 hours, then cooled to room temperature and poured in methanol. The residue obtained after evaporation of the solvent under reduced pressure was dissolved in dry tetrahydrofuran (3 ml) and the solution was dropwise added, at room temperature, with borane methylsulfide (97 ml; 1.02 mmoles), then the reaction mixture was heated to reflux for 1.5 hours. After cooling to room temperature further borane methylsulfide (65 ml; 0.68 mmole) was added. The reaction mixture was heated again to reflux for 1.5 hours. After cooling to 5° C. a 1:1 mixture of acetic acid and water (3 ml) was dropwise added, then the reaction mixture was heated again to reflux for 40 minutes. The residue obtained after evaporation of the solvents under reduced pressure was dissolved in methanol and the solution was evaporated to dryness. The resulting crude was purified by silica gel chromatography (eluent: methylene chloride:methanol:30% ammonia in a gradient fiom 95:5:0.5 to 90:10:1).

There were obtained 44 mg of (S)-N-propyl-N-{6-[2-(4-methylsulfonylphenyl)-ethylamino]hexyl}-5-hydroxymethyl-6-hydroxy-1,2,3,4-tetrahydro-2-naphthylamine.

$^1$H-NMR (200 MHz, CDCl$_3$) δ (ppm): 0.85 (t, 3H); 1.21–2.04 (m, 12H); 2.42–2.92 (m, 15H); 3.01 (s, 3H); 4.82 and 4.86 (2d, 2H, AB system); 6.62 (d, 1H); 6.84 (d, 1H); 7.35–7.85 (m, 4H). Mass (thermospray): 517 (M+H)$^+$.

EXAMPLE 14

Tests of Dopaminergic Activity on Isolated Tissues

Evaluation of the $D_1$ Activity on the Rabbit Splenic Artery (RSA)

Artery rings were prepared according to Semeraro et al., Naunyn. Schnied. Arch. Pharmacol., 1990, 342, 539. These were contracted with U46619 ( 9,11-dideoxy-11$_\alpha$,9$_\alpha$-epoxymethanprostaglandine $F_{2\alpha}$) at a submaximal concentration of 0.1M. The tested compounds were cumulatively administered.

As reference compound (S)-N-propyl-N-{6-[2-(2-methoxyphenoxy)-ethylamino]-hexyl}-5,6-dihydroxy-1,2,3,4-tetrahydro-2-naphthylamine dihydrochloride (Ref. A), described in example 6 of the international patent application No. WO 93/19036 was employed. Furthermore a compound of the invention was compared with its corresponding compound having in 5-position a hydroxy group in the place of a hydroxymethyl group. i.e. Compound 22 of the international patent application No. WO 96/08228, (S)-N-propyl-N-{6-[2-(4-methylsulfonylphenyl)-ethylamino]hexyl}-5,6-dihydroxy-1,2,3,4-tetrahydro-2-naphthylamine dihydrobromide (Ref. B). The agonistic activity was evaluated at the peak of the effect and expressed as potency ratio ($EC_{50}$ of Ref. A/$EC_{50}$ of the tested compound), as shown in Table 1.

Evaluation of the $D_2$ Activity in the Rabbit Ear Artery (REA)

Artery rings were prepared following the method described by Steinsland et al., Science, 1978, 443, 199, modified as follows.

Male New Zealand rabbits (weighing 2.5–3 Kg) were sacrificed by a pentobarbital intravenous injection and bled. The central ear artery was cut into 3 mm-rings. The samples were placed into a 25 ml-bath containing a Krebs solution (mM/l): sodium chloride 118, potassium chloride 4.7, calcium chloride 2.5, magnesium sulphate 1.2, sodium hydrogenocarbonate 25, potassium biphosphate 1.2, glucose 11.1, balanced with oxygen 95%/carbon dioxide 5% and maintained at 35±1° C. The Krebs solution was added with EDTA (10 μM) to present the cathecolamine oxidation, with desipramine (0.1 μM) and corticosterone (30 μM) to stop the neuronal and extraneuronal cathecolamine re-uptake.

The samples were electrically stimulated (10 Hz, 1 msec., 40–80 mA, 500 msec long) at intervals of 5 minutes.

The tested compounds were cumulatively administered.

As reference compounds the reference compounds A and B above were employed.

The agonistic activity was evaluated at the peak of the effect and expressed as potency ratio ($EC_{50}$ of Ref. A/$EC_{50}$ of the tested compound), as shown in Table 1.

TABLE 1

$D_1$ and $D_2$ activity of the compound of Example 7 and of the reference compounds A and B determined by the RSA and REA tests respectively, expressed as potency ratio ($EC_{50}$ of Ref. A/$EC_{50}$ of the tested compound)

|  | $D_1$ activity (RSA) | $D_2$ activity (REA) |
|---|---|---|
| Ref. A | 1 | 1 |
| Ref. B | 50 | 3.3 |
| Example 7 | 2.5 | 1.25 |

These data showed that the compounds of formula II, object of the present invention, have a noticeable dopaminerginc activity at least comparable with the one of the reference compound A.

EXAMPLE 14

Dopaminergic Activity in Vivo Tests

Evaluation of the Hypotensive Activity in the Dog

Beagle dogs were anhaestetized with sodium pentobarbital (30 mg/kg i.v.) and a catheter was put in their carotid artery to measure the blood pressure. The catheter was connected with a pressure transductor. The compounds were administered by a catheter put in the duodenum. The effect on the average blood pressure is expressed as average effect with respect to the test time ($E_{avg}=AUC_{0-360}$/minutes) according to what described by Fettner S. H. et al., Eur. J. Clin. Pharmacol., 48:351–359, 1995. As reference compound the reference compound B above (Ref. B) was used. The controls were treated with the vehicle only.

The doses used for the oral administration were selected on the basis of the hypotensive activity data obtained after intravenous administration.

For evaluating the bioavailability the compounds were thus orally administered in dose equally active with respect to the intravenous administration, i.e. 184 nmoles/kg for the compound of the invention an 5.52 nmoles/kg for the reference one (Ref. B).

The results are set forth in FIG. 1 and show how the compounds of formula II object of the present invention are able to decrease the blood pressure more effectively. For example, the compound of Example 13 showed an average effect of −17.4±3.0 mmHg with respect of −3.5±3.9 mmHg of the reference compound B.

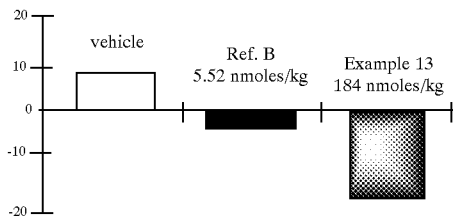

Evaluation of the Absolute Oral Bioavailability

Four Beagle dogs were intramuscularly treated with 20 mg of domperidone (to avoid emesis) and, after 60 minutes, with a bolus of 0.2 mg/kg of a solution of the compound of example 13. The solution of this compound was prepared by dissolving 10 mg thereof in 100 μl of ethanol and 380 μl of 0.1N HCl, the resulting solution being brought to 10 ml with water. Appropriate volumes of this solution were administered to obtain the desired dose based on the dog weight.

Venous blood sample (3 ml) were collected before drug administration and the following times after dosing: 2.5, 5, 10, 15, 20, 30, 45, 60, 90, 120, 180, 240, 300 and 360 minutes.

After a washout period of 7 days, the same 4 Beagle dogs were intramuscularly treated with 20 mg of domperidone and, after 60 minutes, orally treated by gavage with the compound of Example 13 at the dose of 1 mg/kg.

Venous blood samples (3 ml) were collected from the cephalic vein before dosing and at the following times afterwards: 5, 10, 20, 30, 45, 60, 90, 120, 180, 240, 300, 360, 420 minutes and at 24 hours.

The following pharmacokinetic parameters were determined by non-compartmental analysis from the individual plasma concentration of the compound of Example 13:

$C_{max}$, the highest raw data point in the plasma concentration vs time profile;

$t_{max}$, the time equivalent to the highest raw data point in plasma concentration vs time profile;

$AUC_{(0-t)}$, the area under the plasma concentration-time curve between time zero and the last concentration observed, estimated by the linear trapezoidal rule;

Absolute bioavailability (F), the percentage of oral dose that is systemically available, calculated according to the following equation:

$$F(\%) = \frac{DOSE_{intravenous}}{AUC_{intravenous}} \cdot \frac{AUC_{oral}}{DOSE_{oral}} \cdot 100$$

Non-detectable concentrations were put to zero in the calculation of both means plasma concentrations and individual pharmacokinetic parameters.

The absolute oral biovailability of the compound of Example 13 was found to be of 38.8±7.2% (range 28–43%).

What is claimed is:

1. An oral pharmaceutical composition suitable for the treatment of cardiovascular diseases, comprising a therapeutically effective amount of a compound of formula (II)

(II)

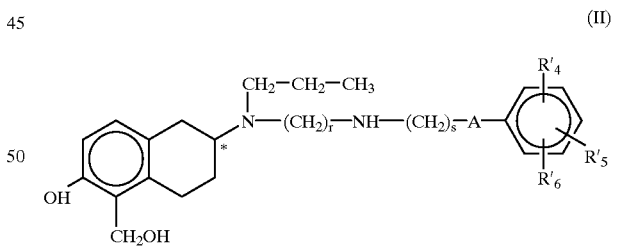

wherein r is an integer selected from 5, 6 and 7;

s is an integer selected from 2 and 3;

A is O or a single bond;

$R'_4$, $R'_5$ and $R'_6$, the same or different, are hydrogen, OH, halogen, nitro, $C_1$–$C_4$ alkyl, $C_1$–$C_4$ alkoxy, $C_1$–$C_4$ alkylthio, $NH_2$, mono- or di-$C_1$–$C_4$ alkylamino, SH, $C_1$–$C_4$ alkylsulfonyl, $C_1$–$C_4$ alkoxycarbonyl, NHCHO, $C_1$–$C_4$ alkycarbonyl-amino, $NHCONH_2$, $C_1$–$C_4$ alkylsulfonylamino, $C_1$–$C_4$ alkylaminosulfonyl, $SO_2NH_2$, $NHSO_2NH_2$, COOH, $SO_3H$, $CONH_2$, $CH_2OH$, or phenyl; or R'$_4$ and R'$_5$, in ortho position relative to each other, together form a chain of 3 or 4 groups selected from CT'T", CO, S, O and NT'", wherein T' is a hydrogen atom or a C$_1$–C$_4$ alkyl group, T" is a hydrogen atom, a C$_1$–C$_4$ alkyl group or an amino group and T'" is a hydrogen atom or a C$_1$–C$_4$ alkyl group; or T' together with a neighbouring T" or T'" forms a single bond, or T'" together with a neighbouring T' or T'" forms a single bond;

the asterisk marks an asymmetric carbon atom;

or a pharmaceutically acceptable salt thereof, in admixture with a pharmaceutically acceptable carrier.

2. The composition according to claim 1, wherein the carbon atom marked by an asterisk has the S configuration.

3. The composition according to claim 1, wherein r is 6 and the carbon atom marked by an asterisk has the S configuration.

4. A process for preparing a compound of formula (II)

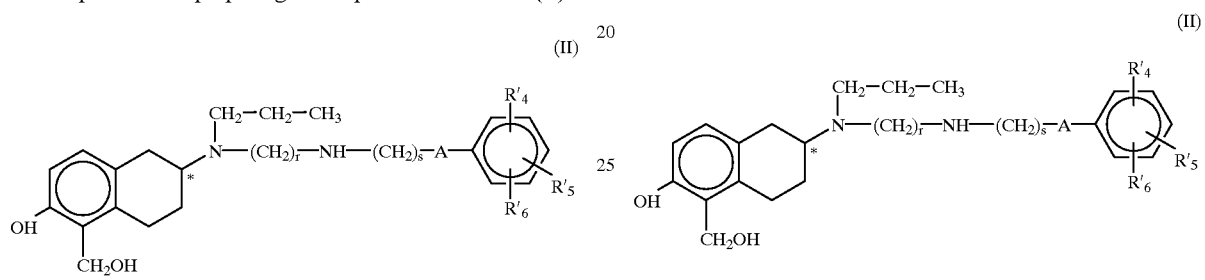

(II)

wherein
r is an integer selected from 5, 6 and 7;
s is an integer selected from 2 and 3;
A is O or a single bond;
R'$_4$, R'$_5$ and R'$_6$, the same or different, are hydrogen, OH, halogen, nitro, C$_1$–C$_4$ alkyl, C$_1$–C$_4$ alkoxy, C$_1$–C$_4$ alkylthio, NH$_2$, mono- or di-C$_1$–C$_4$ alkylamino, SH, C$_1$–C$_4$alkylsulfonyl, C$_1$–C$_4$alkoxycarbonyl, NHCHO, C$_1$–C$_4$ alkycarbonyl-amino, NHCONH$_2$, C$_1$–C$_4$ alkylsulfonylamino, C$_1$–C$_4$ alkylaminosulfonyl, SO$_2$NH$_2$, NHSO$_2$NH$_2$, COOH, SO$_3$H, CONH$_2$, CH$_2$OH, or phenyl; or R'$_4$ and R'$_5$, in ortho position relative to each other, together form a chain of 3 or 4 groups selected from CT'T", CO, S, O and NT'", wherein T' is a hydrogen atom or a C$_1$–C$_4$ alkyl group, T" is a hydrogen atom, a C$_1$–C$_4$ alkyl group or an amino group and T'" is a hydrogen atom or a C$_1$–C$_4$ alkyl group; or T' together with a neighbouring T" or T'" forms a single bond, or T'" together with a neighbouring T' or T'" forms a single bond; and the asterisk marks an asymmetric carbon atom, the process comprising deprotecting and subsequently reducing a compound of formula (VIII)

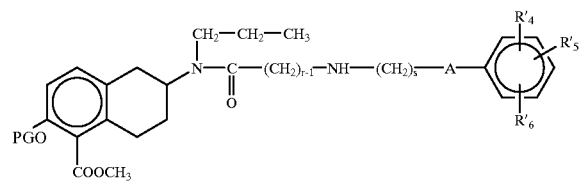

(VIII)

wherein r, s, A, R'$_4$, R'$_5$ and R'$_6$ are as defined above, and PG is a protecting group.

5. A method of treating a cardiovascular disease in a patient in need thereof, comprising orally administering to the patient a cardiovascular disease treating effective amount of a compound of formula (II)

(II)

wherein
r is an integer selected from 5, 6 and 7;
s is an integer selected from 2 and 3;
A is O or a single bond;
R'$_4$, R'$_5$ and R'$_6$, the same or different, are hydrogen, OH, halogen, nitro, C$_1$–C$_4$ alkyl, C$_1$–C$_4$ alkoxy, C$_1$–C$_4$ alkylthio, NH$_2$, mono- or di-C$_1$–C$_4$ alkylamino, SH, C$_1$–C$_4$ alkylsulfonyl, C$_1$–C$_4$ alkoxycarbonyl, NHCHO, C$_1$–C$_4$ alkylcarbonyl-amino, NHCONH$_2$, C$_1$–C$_4$ alkylsulfonylamino, C$_1$–C$_4$ alkylaminosulfonyl, SO$_2$NH$_2$, NHSO$_2$NH$_2$, COOH, SO$_3$H, CONH$_2$, CH$_2$OH, or phenyl; or R'$_4$ and R'$_5$, in ortho position relative to each other, together form a chain of 3 or 4 groups selected from CT'T", CO, S, O and NT'", wherein T' is a hydrogen atom or a C$_1$–C$_4$ alkyl group, T" is a hydrogen atom, a C$_1$–C$_4$ alkyl group or an amino group and T'" is a hydrogen atom or a C$_1$–C$_4$ alkyl group; or T' together with a neighbouring T" or T'" forms a single bond, or T'" together with a neighbouring T' or T'" forms a single bond;

the asterisk marks an asymmetric carbon atom;
or a pharmaceutically acceptable salt thereof.

* * * * *

UNITED STATES PATENT AND TRADEMARK OFFICE
CERTIFICATE OF CORRECTION

PATENT NO. : 6,232,348 B1  Page 1 of 1
DATED : May 15, 2001
INVENTOR(S) : Stefania Montanari et al.

It is certified that error appears in the above-identified patent and that said Letters Patent is hereby corrected as shown below:

<u>Title page,</u>
Item [75], please change "Milan" to -- Vicenza --.

Signed and Sealed this

Fifth Day of February, 2002

Attest:

JAMES E. ROGAN
*Director of the United States Patent and Trademark Office*

*Attesting Officer*